(12) United States Patent
Chono

(10) Patent No.: US 12,737,853 B2
(45) Date of Patent: Sep. 15, 2026

(54) ULTRASOUND DIAGNOSTIC APPARATUS AND IMAGE PROCESSING METHOD

(71) Applicant: FUJIFILM Healthcare Corporation, Kashiwa (JP)

(72) Inventor: Tomoaki Chono, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 680 days.

(21) Appl. No.: 17/744,801

(22) Filed: May 16, 2022

(65) Prior Publication Data

US 2022/0384015 A1 Dec. 1, 2022

(30) Foreign Application Priority Data

May 25, 2021 (JP) ................................. 2021-087802

(51) Int. Cl.

| | |
|---|---|
| ***G06T 5/70*** | (2024.01) |
| ***A61B 8/00*** | (2006.01) |
| ***G06T 7/30*** | (2017.01) |

(52) U.S. Cl.

CPC .............. *G06T 5/70* (2024.01); *A61B 8/5215* (2013.01); *G06T 7/30* (2017.01); *G06T 2207/10132* (2013.01); *G06T 2207/30048* (2013.01)

(58) Field of Classification Search

CPC ........................................... G06T 2207/10132

See application file for complete search history.

(56) References Cited

U.S. PATENT DOCUMENTS

| | | | | |
|---|---|---|---|---|
| 2005/0228276 | A1 | 10/2005 | He et al. | |
| 2012/0078097 | A1 | 3/2012 | Wang et al. | |
| 2013/0182935 | A1 | 7/2013 | Wang et al. | |
| 2018/0279997 | A1* | 10/2018 | Abe | A61B 8/5223 |

FOREIGN PATENT DOCUMENTS

| | | |
|---|---|---|
| JP | 2003-250804 | 9/2003 |
| JP | 2011-000470 | 1/2011 |
| JP | 2013-022462 A | 2/2013 |

OTHER PUBLICATIONS

Schmidt-Richberg et al., "Estimation of slipping organ motion by registration with direction-dependent regularization," Medical Image Analysis, vol. 16, pp. 150-159 (Year: 2012).*

Ma et al., "Lagrangian displacement tracking using a polar grid between endocardial and epicardial contours for cardiac strain imaging," Med. Phys. 39, pp. 1779-1792 (Year: 2012).*

Feb. 6, 2024 Japanese official action (machine translation into English) in connection with Japanese Patent Application No. 2021-087802.

(Continued)

*Primary Examiner* — Vincent Rudolph
*Assistant Examiner* — Meredith Taylor
(74) *Attorney, Agent, or Firm* — Paul Teng

(57) ABSTRACT

An interpolation unit generates a vector array representing a movement destination of a representative point array. A smoothing unit smoothes a tangential component and a normal component of each vector of the vector array, to generate a smoothed vector array. An aligning unit generates a new representative point array based on the smoothed vector array. In this process, alignment is performed for each representative point sequence. A tracking image is created based on the new representative point array.

4 Claims, 14 Drawing Sheets

(56) References Cited

OTHER PUBLICATIONS

Chinese official action dated Jul. 18, 2025 (and English translation thereof) in connection with Chinese Patent Application No. 202210572946.X.
Feb. 28, 2026 Chinese official action (and translation thereof into English) in connection with counterpart Chinese Patent Application No. 202210572946.X.

* cited by examiner

FIG. 1

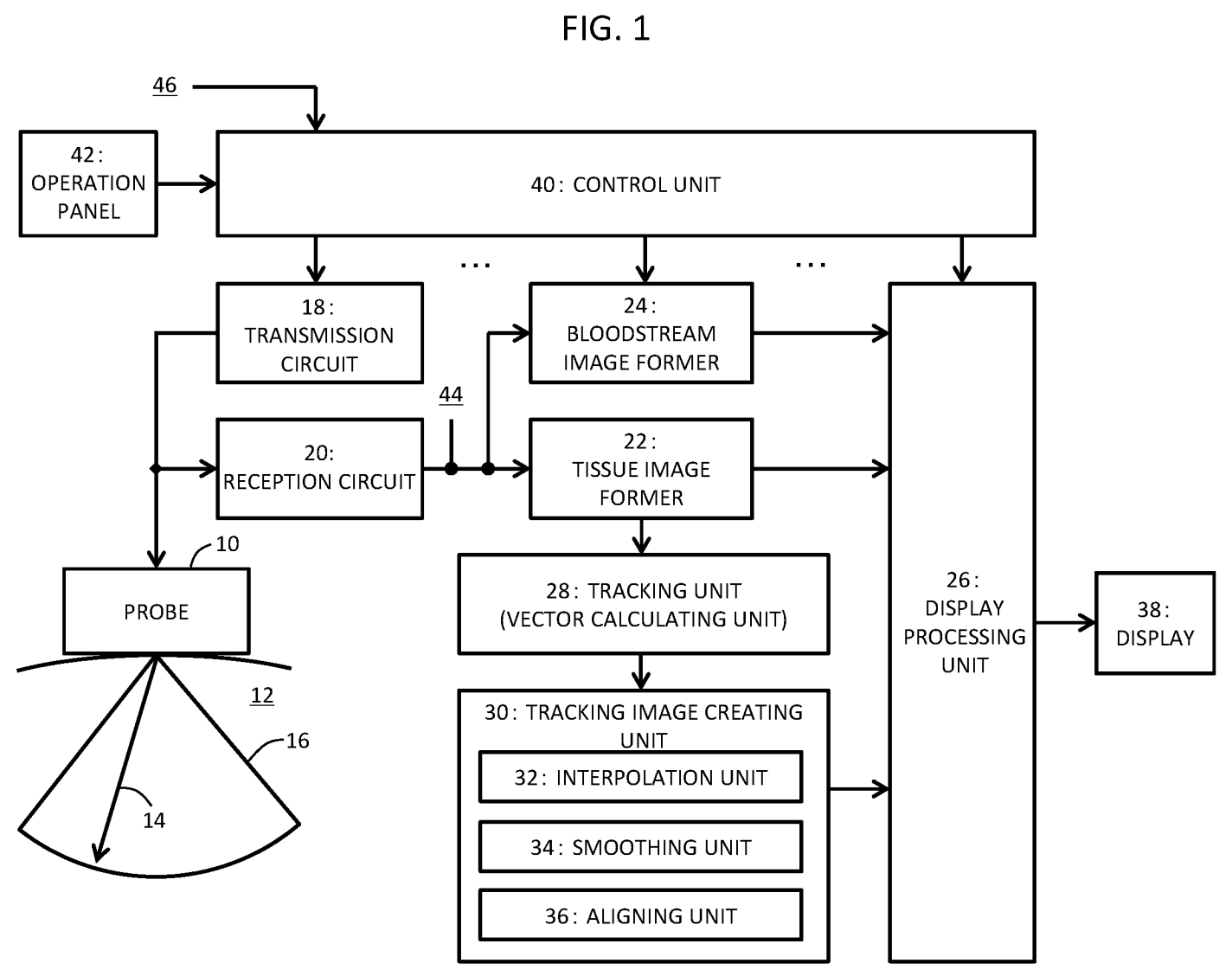

40 : CONTROL UNIT

42 : OPERATION PANEL

46

18 : TRANSMISSION CIRCUIT

20 : RECEPTION CIRCUIT

44

24 : BLOODSTREAM IMAGE FORMER

22 : TISSUE IMAGE FORMER

28 : TRACKING UNIT (VECTOR CALCULATING UNIT)

30 : TRACKING IMAGE CREATING UNIT

32 : INTERPOLATION UNIT

34 : SMOOTHING UNIT

36 : ALIGNING UNIT

26 : DISPLAY PROCESSING UNIT

38 : DISPLAY

PROBE

10

12

14

16

60
62
70
68
64(66)
74A
74
67

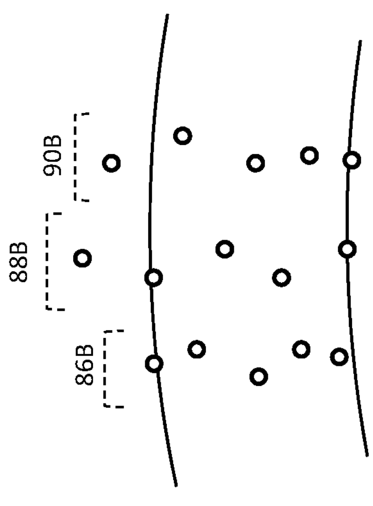
FIG. 5
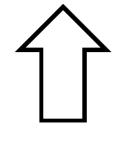
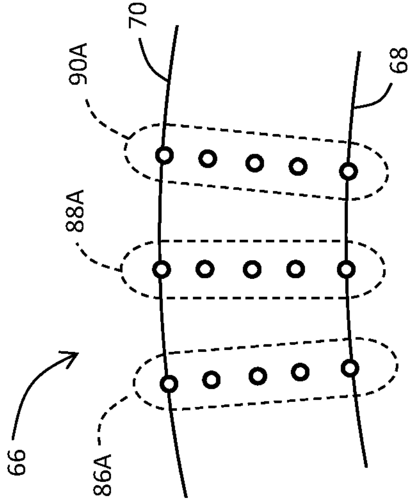

START
SELECT INITIAL FRAME
S10
SET INITIAL REPRESENTATIVE POINT ARRAY
S12
S14
COMPLETED?
Y
N
END
TRACK BETWEEN FRAMES
S16
DECOMPOSE INTO TWO COMPONENTS
S18
SMOOTH
S20
ALIGN
S22
FORM TRACKING IMAGE
S24

ULTRASOUND DIAGNOSTIC APPARATUS AND IMAGE PROCESSING METHOD

CROSS REFERENCE TO RELATED APPLICATION

This application claims priority to Japanese Patent Application No. 2021-087802 filed on May 25, 2021, which is incorporated herein by reference in its entirety including the specification, claims, drawings, and abstract.

TECHNICAL FIELD

The present disclosure relates to an ultrasound diagnostic apparatus and an image processing method, and in particular to a cardiac muscle tracking technique.

BACKGROUND

For evaluating a state or a function of a heart of an examination target, an ultrasound examination using an ultrasound diagnostic apparatus is performed. For example, a frame data sequence is acquired from a predetermined cross section of the heart, and a tomographic image sequence is generated and displayed as a video image based on the frame data sequence. A cardiac muscle (cardiac wall) tracking technique is applied to the tomographic image sequence, and, as a consequence, a tracking image is generated for each tomographic image. The tracking image is displayed in an overlapping manner over each tomographic image (for example, refer to JP 2003-250804 A and JP 2011-470 A).

The tracking image is formed from, for example, a marker array representing a plurality of tracking points which are set over an entirety of a cardiac muscle region. Based on a dynamic change of the marker array, a motion of each individual tracking point; that is, a motion of each individual cardiac muscle site, can be recognized, evaluated, and measured.

An ultrasound image includes noise such as an artifact. The noise may cause a tracking error. Specifically, phenomena may occur in which, with the elapse of time, an alignment state is disturbed at a portion of the marker array being displayed, or a portion of the marker array may deviate from the cardiac muscle region, possibly causing an unnatural motion. Such phenomena become obstacles for the ultrasound examination.

An advantage of the present disclosure lies in improvement of quality of the tracking image. Alternatively, an advantage of the present disclosure lies in suppression of disturbance and deviation in the tracking image.

SUMMARY

According to one aspect of the present disclosure, there is provided an ultrasound diagnostic apparatus comprising: a tracking unit that calculates an (n−1)th vector array (wherein n=1, 2, 3, . . . ) representing a movement destination of an (n−1)th representative point array which is set for a cardiac muscle region between an (n−1)th frame and an nth frame; a smoothing unit that smoothes the (n−1)th vector array, to thereby generate an (n−1)th smoothed vector array; an aligning unit that aligns, when an nth representative point array formed from a plurality of representative point sequences arranged in a cardiac muscle contour direction is generated based on the (n−1)th smoothed vector array, each representative point sequence of the nth representative point array along a direction intersecting the cardiac muscle contour direction; and a creation unit that creates a tracking image based on the nth representative point array.

According to another aspect of the present disclosure, there is provided a method of processing an image, the method comprising: calculating an (n−1)th vector array (wherein n=1, 2, 3, . . . ) representing a movement destination of an (n−1)th representative point array which is set for a cardiac muscle region, based on (n−1)th frame data and nth frame data acquired by transmission and reception of ultrasound; smoothing the (n−1)th vector array, to thereby generate an (n−1)th smoothed vector array; aligning, when an nth representative point array formed from a plurality of representative point sequences arranged in a cardiac muscle contour direction is generated based on the (n−1)th smoothed vector array, each representative point sequence of the nth representative point array along a direction intersecting the cardiac muscle contour direction; and creating a tracking image based on the nth representative point array.

BRIEF DESCRIPTION OF DRAWINGS

Embodiment(s) of the present disclosure will be described based on the following figures, wherein:

FIG. 1 is a block diagram showing a structure of an ultrasound diagnostic apparatus according to an embodiment of the present disclosure;

FIG. 5 is a diagram showing disturbance and deviation in a representative point array;

FIG. 6 is a diagram showing a vector array calculated between frames;

FIG. 10 is a diagram showing a vector sequence after components are separated;

FIG. 13 is a diagram showing details of determination of a movement destination, in relation to the first alignment method;

DESCRIPTION OF EMBODIMENTS

Figure 2:
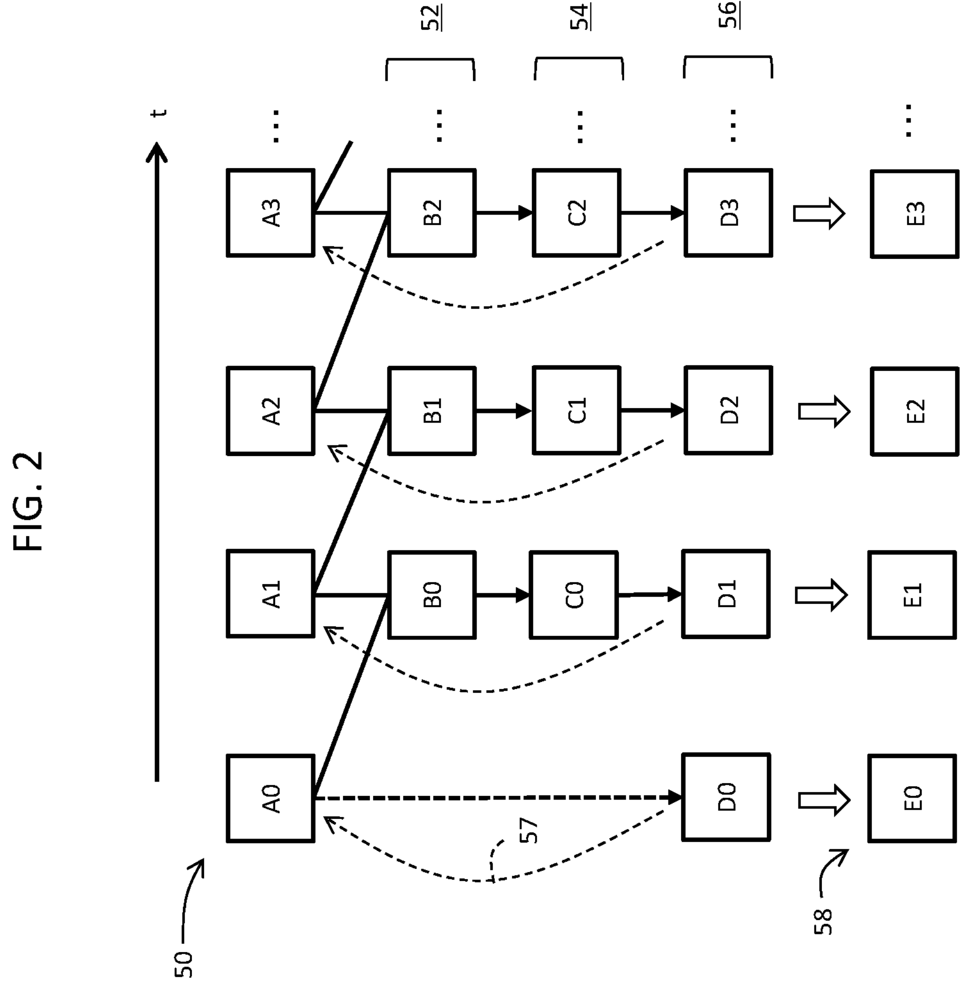
FIG. 2 is a diagram showing processing of a display frame data sequence.

An embodiment of the present disclosure will now be described with reference to the drawings.

(1) Overview of Embodiment

An ultrasound diagnostic apparatus according to an embodiment of the present disclosure comprises a tracking unit, a smoothing unit, and an aligning unit. The tracking unit calculates an (n−1)th vector array (wherein n=1, 2, 3, . . . ) representing a movement destination of an (n−1)th representative point array which is set for a cardiac muscle region between an (n−1)th frame and an nth frame. The smoothing unit smoothes the (n−1)th vector array, to thereby generate an (n−1)th smoothed vector array. The aligning unit aligns, when an nth representative point array formed from a plurality of representative point sequences arranged in a cardiac muscle contour direction is generated based on the (n−1)th smoothed vector array, each representative point sequence of the nth representative point array along a direction intersecting the cardiac muscle contour direction. A creation unit creates a tracking image based on the nth representative point array. The tracking unit corresponds to a calculator or a vector calculator. The smoothing unit corresponds to a smoother. The aligning unit corresponds to an aligner.

According to the structure described above, the vector array is smoothed, and then, a new representative point array is generated based on the smoothed vector array. In this process, each representative point sequence is aligned. With the combination of the smoothing and the aligning, the tracking image becomes less likely to be affected by noise. In particular, unnatural disturbance and deviation in the tracking image can be effectively suppressed.

The (n−1)th frame is a preceding frame, and the nth frame is a subsequent frame. The smoothing is spatial smoothing, but alternatively, temporal smoothing may be additionally employed. After the aligning, the arrangements of the plurality of representative points of each representative point sequence may be completely aligned, or approximately aligned. Each representative point may be directly tracked, or indirectly tracked.

In an embodiment of the present disclosure, the smoothing unit generates the (n−1)th smoothed vector array by calculating a smoothed tangential component and a smoothed normal component forming the smoothed vector for each representative point of interest in the (n−1)th representative point array based on the (n−1)th vector array.

By applying the smoothing for each component after the components are separated, the calculation for the smoothing can be simplified. By smoothing in the tangential direction, a local disturbance in the cardiac muscle contour direction in the representative point array can be suppressed. By smoothing in the normal direction, local disturbance in a cardiac muscle transverse direction in the representative point array can be suppressed.

In an embodiment of the present disclosure, the smoothing unit sets a group of representative points formed from a plurality of representative points arranged along the cardiac muscle contour direction, the group of representative points including the representative point of interest. The smoothing unit smoothes a plurality of tangential components of a group of vectors belonging to the group of representative points, to calculate the smoothed tangential component for the representative point of interest, and smoothes a plurality of normal components of a group of vectors belonging to the group of representative points, to calculate the smoothed normal component for the representative point of interest. A plurality of groups of representative points which are arranged in the cardiac muscle transverse direction are set for each of the representative point sequences.

In general, in the cardiac muscle, motions of a plurality of positions (or a plurality of layers) in the cardiac muscle transverse direction are not uniform, and differ for each position (or layer). In consideration of this, the above-described structure defines a reference range (group of representative points) elongated along the cardiac muscle contour direction, for each position in the cardiac muscle transverse direction. Based on the plurality of tangential components and the plurality of normal components of the group of representative points, the tangential component and the normal component for the representative point of interest are individually smoothed. With this process, the motion of each representative point may be made smooth, and the local disturbance for the representative point array as a whole can be suppressed. In an embodiment of the present disclosure, the group of representative points is a one-dimensional row of representative points.

In an embodiment of the present disclosure, the aligning unit aligns, for each representative point sequence of the (n−1)th representative point array, movement destinations of a plurality of representative points of the representative point sequence based on a smoothed vector sequence belonging to the representative point sequence or a smoothed tangential component sequence thereof, to thereby generate the nth representative point array. According to this structure, the movement destination is aligned for each representative point sequence. The representative point sequence thus moves collectively while maintaining the aligned state.

In an embodiment of the present disclosure, the aligning unit calculates, for each representative point sequence of the (n−1)th representative point array, a target line based on a smoothed vector sequence belonging to the representative point sequence or a smoothed tangential component sequence thereof. The aligning unit determines, for each representative point sequence of the (n−1)th representative point array, movement destinations of a plurality of representative points of the representative point sequence on or near the target line, to thereby generate the nth representative point array.

According to the above-described structure, the movement destination of each representative point sequence is determined according to a target line. Thus, the aligned state of each representative point sequence is maintained after the movement. The target line may be determined based on the smoothed vector sequence or based on a tangential component sequence of the smoothed vector sequence. Alternatively, a plurality of new representative points may be set by correcting each tangential component according to the target line, and setting the representative points at a plurality of positioned shown by a plurality of vectors after the correction. The target line is a straight line or a curved line. Alternatively, the target line may be determined through linear regression based on a method of least squares.

A method of processing an image according to an embodiment of the present disclosure comprises a tracking step, a smoothing step, an aligning step, and a creating step. In the tracking step, an (n−1)th vector array (wherein n=1, 2, 3, . . . ) representing a movement destination of an (n−1)th representative point array which is set for a cardiac muscle region is calculated based on (n−1)th frame data and nth frame data acquired by transmission and reception of ultrasound. In the smoothing step, the (n−1)th vector array is smoothed, to thereby generate an (n−1)th smoothed vector array. In the aligning step, when an nth representative point array formed from a plurality of representative point sequences arranged in a cardiac muscle contour direction is generated based on the (n−1)th smoothed vector array, each representative point sequence of the nth representative point array is aligned along a direction intersecting the cardiac muscle contour direction. In the creating step, a tracking image is created based on the nth representative point array.

The above-described method of processing the image is executed by an information processing apparatus having a processor which executes a program. The information processing apparatus is a concept including an ultrasound diagnostic apparatus, an image processing apparatus, a computer, and the like. The program is installed to the information processing apparatus through a transportable recording medium or via a network. In the information processing apparatus, the program is stored in a non-transitory recording medium.

(2) Details of Embodiment

FIG. 1 shows a structure of an ultrasound diagnostic apparatus according to an embodiment of the present disclosure. The ultrasound diagnostic apparatus is a medical apparatus which is equipped in a medical organization, and which forms an ultrasound image based on data acquired by transmission of ultrasound to an examination target and reception of a reflected wave. In the ultrasound diagnostic apparatus, a portion for processing a display frame data sequence to be described below corresponds to the information processing apparatus and the image processing apparatus.

A probe 10 is a transportable transmission and reception device. The probe 10 is caused to contact a surface of an examination target 12. The probe 10 includes a transducer array formed from a plurality of transducers. An ultrasound beam 14 is formed by the transducer array. The ultrasound beam 14 is electrically and repetitiously scanned, to thereby repetitiously form a beam scanning plane 16. As a method of electronic scanning, there are known an electronic sector scanning method, an electronic linear scanning method, and the like. Alternatively, a 2D transducer array formed from a plurality of transducers arranged two-dimensionally may be provided in the probe 10.

During transmission, a transmission circuit 18 supplies a plurality of transmission signals in parallel to each other to the transducer array. As a consequence, a transmission beam is formed. During reception, a reflected wave from within a living body is received by the transducer array, and a plurality of reception signals are output in parallel to each other from the transducer array to a reception circuit 20. In the reception circuit 20, a phase-alignment and summing (delay and summing) process is applied to the plurality of reception signals. With this process, reception beam data are generated.

A reception frame data sequence is output from the reception circuit 20. The reception frame data sequence is formed from a plurality of sets of reception frame data arranged on a time axis. Each set of reception frame data is formed from a plurality of sets of reception beam data arranged in an electronic scanning direction. Each set of reception beam data is formed from a plurality of sets of echo data arranged in a depth direction.

A beam data processing circuit is provided downstream of the reception circuit 20, but illustration of the beam data processing circuit is omitted. The reception frame data sequence is sent to a tissue image former 22. The reception frame data sequence is also sent to a bloodstream image former 24 as necessary.

The tissue image former 22 is a module which generates a display frame data sequence from the reception frame data sequence. The display frame data sequence forms a tomographic image sequence serving as a video image. More specifically, the tissue image former 22 has a digital scan converter (DSC) serving as a processor having a coordinate conversion function, a pixel interpolation function, a frame rate conversion function, or the like. The display frame data sequence is sent to a display processing unit 26, and also to a tracking unit 28.

The bloodstream image former 24 is a module which forms a bloodstream image sequence as the display frame data sequence based on Doppler information included in the reception frame data sequence. The bloodstream image former 24 also has a DSC. In a color flow mapping (CFM) mode, a combined image formed from a black-and-white tomographic image and a color bloodstream image is displayed on a display 38 to be described later.

In a tracking mode (tracking image display mode), the tracking unit 28 and a tracking image creating unit 30 function. The tracking unit 28 executes tracking for each tracking point between frame data adjacent in time (or simply "between frames"), and calculates a two-dimensional movement vector for each tracking point. In the following, the two-dimensional movement vector will simply be referred to as a "vector". More specifically, the tracking unit 28 sets an intersection array as a grid or a mesh for each set of individual display frame data. After the intersection array is set, the tracking unit 28 executes inter-frame tracking for each individual intersection, and calculates the vector for each individual intersection. With this process, a vector array representing motions of a plurality of intersections is generated for each set of display frame data.

In the illustrated example structure, the tracking image creating unit 30 includes an interpolation unit 32, a smoothing unit 34, and an aligning unit 36. In the present embodiment, an initial representative point array is set on an initial frame, on a cardiac muscle region in the initial frame. The representative point array is formed from a plurality of representative point sequences arranged along a cardiac muscle contour direction. Each individual representative point sequence is formed from a plurality of representative points (5 representative points in the present embodiment) arranged along a direction intersecting the cardiac muscle contour direction (typically, a cardiac muscle transverse direction).

The interpolation unit 32 generates a vector array representing a movement destination of the representative point array for each frame pair adjacent in time (between frames), based on a vector array representing a movement destination of the intersection array. In this process, for each representative point, the vector is indirectly calculated through weighted interpolation based on a plurality of vectors near the representative point. Alternatively, the representative point itself may be set as the tracking point.

The smoothing unit 34 smoothes the vector array generated by the interpolation unit 32, to generate a smoothed vector array. For the smoothing process, component separation is first executed for each individual vector; that is, a tangential component and a normal component are calculated for each individual vector. Then, the smoothing process is executed for each component within a predetermined reference range. This process will be described later in detail.

The aligning unit 36 generates a new representative point array after alignment, based on the smoothed vector array; that is, a tangential component array after the smoothing and a normal component array after the smoothing. By combining the smoothing and aligning processes, it becomes possible to suppress local deviation and fluctuation of the representative point array from the cardiac muscle region. The aligning process will be described later in detail.

The tracking image creating unit 30 generates a tracking image based on the new representative point array after the alignment. The tracking image is formed from a plurality of markers representing a plurality of representative points. More specifically, the tracking image is formed from a plurality of marker sequences arranged along the cardiac muscle contour direction. Each marker sequence is formed from a plurality of markers arranged along a direction intersecting the cardiac muscle contour direction. Each marker is a display element. Data representing the tracking image are output from the tracking image creating unit 30 to the display processing unit 26.

A display frame data pair adjacent in time is formed from (n−1)th display frame data (preceding frame data) and nth display frame data (subsequent frame data). Here, n is an integer greater than or equal to 1. Between the display frame data, an (n−1)th vector array is generated, and an (n−1)th smoothed vector array is generated from the (n−1)th vector array. An nth representative point array is generated based on the (n−1)th smoothed vector array, and an nth tracking image is generated based on the nth representative point array. Alternatively, the processes such as tracking may be applied to the reception frame data sequence in place of the display frame data sequence.

Each of the tracking unit 28, the tracking image creating unit 30, and the display processing unit 26 is formed from a processor. The tracking unit 28, the tracking image creating unit 30, and the display processing unit 26 may be formed from a single processor, or may be realized as functions of a control unit 40.

The display processing unit 26 has an image combining function, a color processing function, or the like. The tracking image sequence forming a video image is combined to a tomographic image sequence forming a video image. A combined image sequence generated through this process is displayed on the display 38 as a video image. The display 38 is formed from an LCD, an organic EL display device, or the like.

The control unit 40 controls operations of various elements shown in FIG. 1. The control unit 40 is more specifically formed from a processor (CPU) which executes a program. An operation panel 42 is connected to the control unit 40 as an inputting device. In addition, an output signal from an electrocardiograph 46 is sent to the control unit 40.

In the present embodiment, a cine memory 44 is provided between the reception circuit 20 and the tissue image former 22. The cine memory 44 has a ring buffer structure, and stores the reception frame data sequences from the current point in time to a certain period in the past. In a frozen state (a state in which the transmission and reception are stopped), a reception frame data sequence which is read from the cine memory 44 is sent to the tissue image former 22, and a display frame data sequence is generated from the reception frame data sequence. In addition, a tracking image sequence is generated from the display frame data sequence. Alternatively, the tracking image sequence may be formed in a real-time operation state.

FIG. 2 shows an example of image processing. The horizontal axis is a time axis. A display frame data sequence 50 is formed from a plurality of sets of display frame data A0, A1, A2, A3, . . . , arranged in the time axis direction. Of the display frame data, the display frame data A0 is initial display frame data (initial frame). Alternatively, the initial display frame data may be selected based on an electrocardiographic signal.

A vector array sequence 52 is formed from a plurality of vector arrays B0, B1, B2, . . . , generated based on the plurality of sets of display frame data A0, A1, A2, A3, . . . . As already described, one vector array B0, B1, B2, . . . is generated for each display frame data pair adjacent in time.

Each vector array B0, B1, B2, . . . forming the vector array sequence 52 is smoothed, and a smoothed vector array sequence 54 is generated. The smoothed vector array sequence 54 is formed from a plurality of smoothed vector arrays C0, C1, C2, . . . .

A representative point array sequence 56 is formed from representative point arrays D0, D1, D2, D3, . . . , arranged along the time axis. Of the representative point arrays, the representative point array D0 is an initial representative point array which is set on the initial frame. The other representative point arrays D1, D2, D3, . . . , are generated based on a plurality of smoothed vector arrays C0, C1, C2, . . . . More specifically, each of the representative point arrays D1, D2, D3, . . . , has passed through the alignment process.

The initial representative point array D0 is set by a user or is set automatically. As shown by reference numeral 57, with the initial representative point array D0, a tracking target is identified. Similarly, with each of the representative point arrays D1, D2, D3, . . . , a tracking target is identified. A marker array sequence 58 formed from a plurality of marker arrays (a plurality of tracking images) E0, E1, E2, E3, . . . , is generated based on the representative point array sequence 56.

Figure 3:
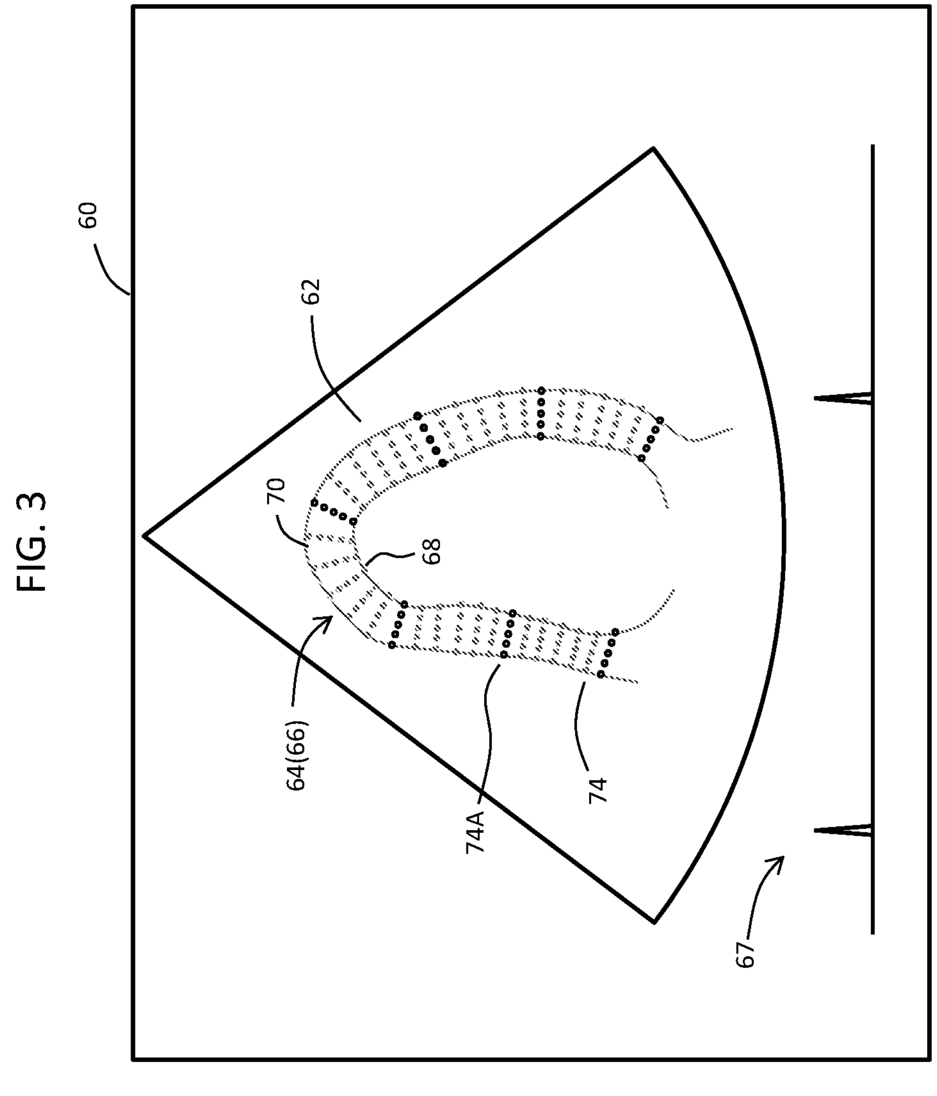
FIG. 3 is a diagram showing a tracking image.

An image process according to the present embodiment will now be described in detail. FIG. 3 shows an initial frame selected by the user in a frozen state. Specifically, a tomographic image 62 is displayed on a screen of the display, and an electrocardiographic waveform 67 is displayed below the tomographic image 62. In the illustrated example, the tomographic image 62 is an image showing a cross section of the left ventricle. Reference numeral 68 shows an inner membrane of the cardiac muscle, and reference numeral 70 shows an outer membrane of the cardiac muscle. A region between the inner membrane 68 and the outer membrane 70 is the cardiac muscle region.

A representative point array 66 is set over an entirety of the cardiac muscle region, and a marker array 64 showing the representative point array 66 is displayed. The representative point array 66 is formed from a plurality of representative point sequences arranged along the cardiac muscle contour direction. Correspondingly, the marker array 64 is formed from a plurality of marker sequences 74 representing a plurality of representative point sequences. Each representative point sequence is formed from a plurality of representative points arranged along a direction intersecting the cardiac muscle contour direction (normally, the cardiac muscle transverse direction in the initial frame). Each marker sequence 74 is formed from a plurality of markers representing a plurality of representative points.

In the setting of the representative point array, a plurality of designated points may first be designated by the user on the inner membrane 68, an inner membrane point sequence formed from many inner membrane points may be automatically generated on the inner membrane based on the plurality of designated points, and each representative point sequence may be automatically determined with each inner membrane point as a base point. When it is difficult to extract or identify the outer membrane 70, the outer membrane 70 may be deduced as a line separated by a certain distance to an outer side from the inner membrane 68. Alternatively, a direction orthogonal to the inner membrane may be identified for each inner membrane point, and a plurality of representative points may be uniformly set in this direction. When the cardiac muscle region is segmented into a plurality of sub-regions, a part of the marker sequences may be displayed with emphasis, so as to clarify boundaries between the sub-regions.

Figure 4:
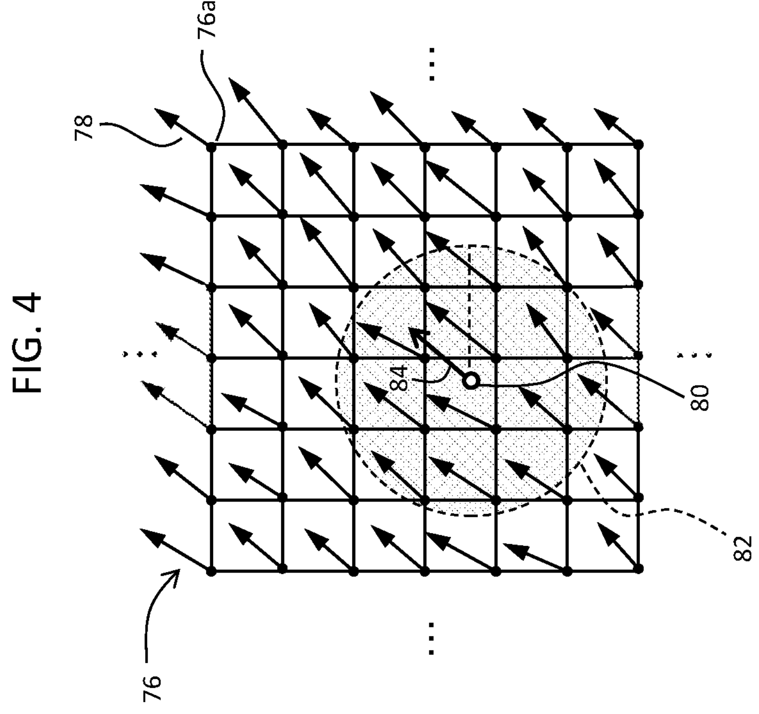
FIG. 4 is a diagram showing a method of calculating a vector for each representative point.

In the present embodiment, as shown in FIG. 4, a grid 76 is set for each individual set of display frame data, and inter-frame tracking is executed for each individual intersection 76*a* defined by the grid 76. With this process, a vector (movement vector) 78 is calculated for each intersection 76*a*. In the inter-frame tracking, known techniques such as pattern matching may be utilized. For each individual set of display frame data, a vector array corresponding to the intersection array is calculated.

When a vector representing a movement destination of a representative point 80 is to be calculated, a reference range 82 centered at the representative point 80 is determined, and reference is made to a group of vectors corresponding to a group of intersections belonging to the reference range 82. A vector 84 for the representative point 80 is determined through weighted interpolation based on the group of vectors. A sequence of processes described above with reference to FIG. 4 is executed for each representative point. With this process, the vector array corresponding to the representative point array is generated.

FIG. 5 shows at the left the representative point array 66 which is set between the inner membrane 68 and the outer membrane 70. Specifically, three representative point sequences 86A, 88A, and 90A are shown. When the inter-frame tracking is progressed without applying any constraint condition, as shown at the right in FIG. 5, forms of the three representative point sequences 86B, 88B, and 90B tend to be easily disturbed, and projection from the cardiac muscle region tends to occur easily. The tomographic image includes a certain amount of noise component (artifact), and the tracking error inevitably tends to occur. The above-described problem arises as a result of the tracking error. Thus, in the present embodiment, as will be described below in detail, smoothing and aligning processes are applied to the vector array generated by the inter-frame tracking.

Figure 6:
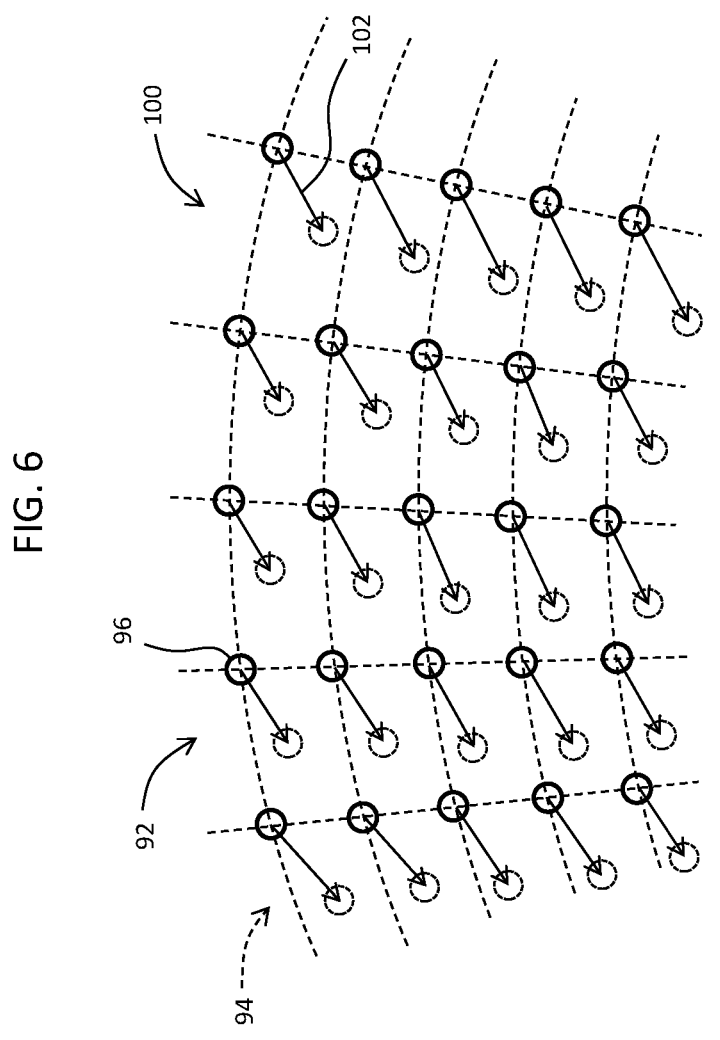

FIG. 6 shows a representative point array 92 which is set on the preceding frame. The representative point array 92 is formed from a plurality of representative points 96. A vector array 100 is generated as a result of tracking between the preceding frame and the subsequent frame. The vector array 100 is formed from a plurality of vectors 102 originating from a plurality of the representative points 96. In FIG. 6, a provisional representative point array 94 on the subsequence frame is shown with a broken line. The vector array 100 may include one or a plurality of vectors caused by the tracking error.

Figure 7:
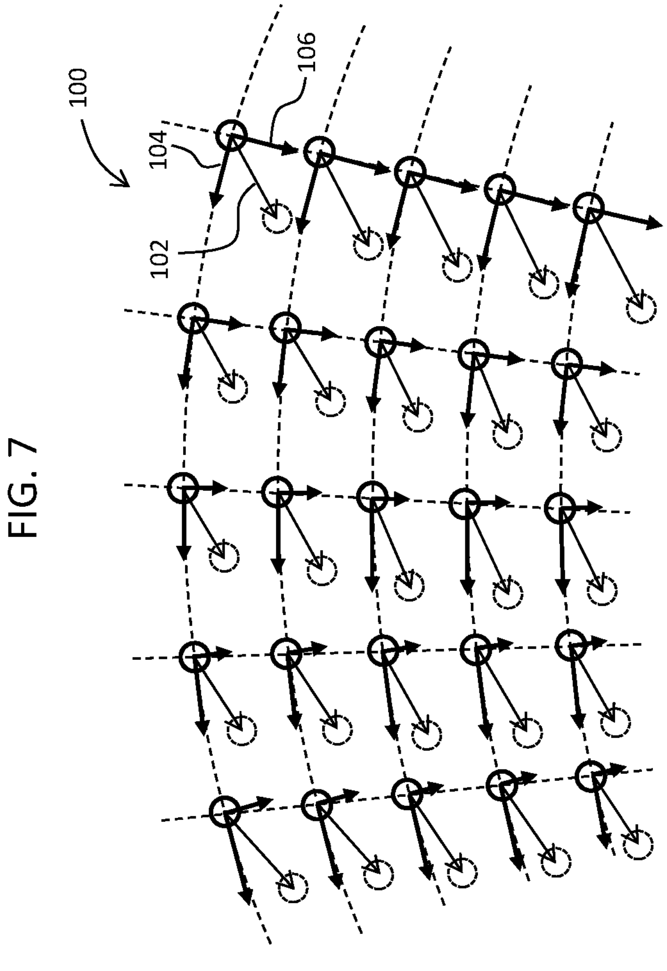
FIG. 7 is a diagram showing a tangential component and a normal component calculated for each vector.

In the smoothing, first, as shown in FIG. 7, component separation is applied to each vector 102 of the vector array 100, and each vector 102 is separated into two components. Specifically, each vector 102 is separated into a tangential component 104 and a normal component 106. The tangential component 104 is a component in a tangential direction, and the normal component 106 is a component in a direction orthogonal to the tangential direction.

Figure 8:
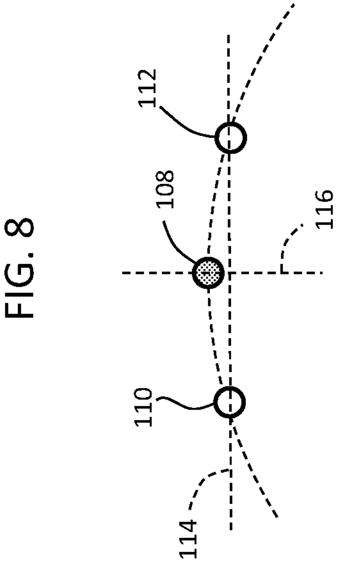
FIG. 8 is a diagram showing a first example calculation in a tangential direction and a normal direction.

For example, as shown in FIG. 8, with a representative point of interest 108 as a reference, two representative points 110 and 112 adjacent in the cardiac muscle contour direction may be identified, and a direction of a straight line 114 passing through these representative points may be set as the tangential direction. Further, a direction of a straight line 116 orthogonal to the straight line 114 may be set as the normal direction.

Figure 9:
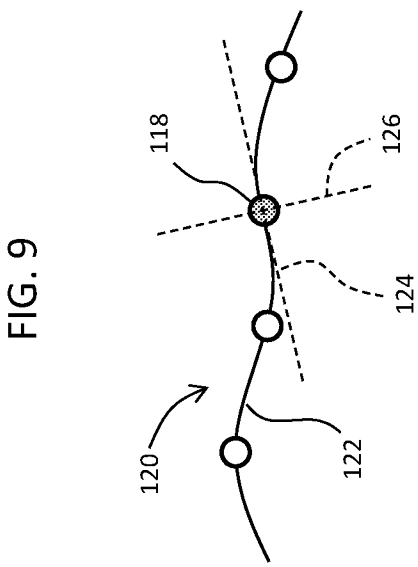
FIG. 9 is a diagram showing a second example calculation in the tangential direction and the normal direction.

Alternatively, as shown in FIG. 9, a curved line 122 may be identified based on a plurality of representative points arranged in the cardiac muscle contour direction, a line of tangent 124 tangential to the curved line 122 at a representative point of interest 118 may be identified, and the direction of the line of tangent may be set as the tangential direction. In this case, a direction of a straight line 126 orthogonal to the tangential line 124 at the representative point of interest 118 may be set as the normal direction.

Figure 10:
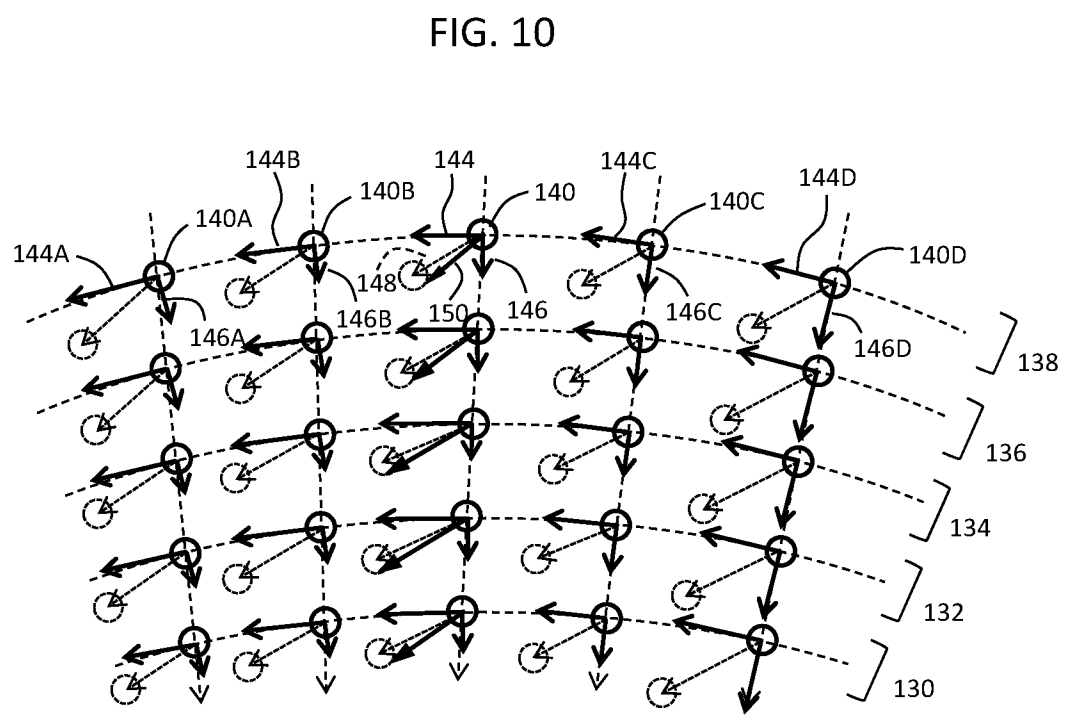

Then, as shown in FIG. 10, with each representative point being set as a representative point of interest, a group of representative points formed from a plurality of representative points arranged along the cardiac muscle contour direction is set for each representative point of interest, and a plurality of tangential components and a plurality of normal components of a group of vectors belonging to the group of representative points are each smoothed. For example, with respect to a representative point of interest 140, a group of representative points 138 formed from a representative point 140A, a representative point 140B, the representative point of interest 140, a representative point 140C, and a representative point 140D is set. After the setting, a smoothed tangential component of the representative point of interest 140 is calculated by averaging a plurality of tangential components 144A, 144B, 144, 144C, and 144D in the group of representative points 138. Similarly, a smoothed normal component of the representative point of interest 140 is calculated by averaging a plurality of normal components 146A, 146B, 146, 146C, and 146D in the group of representative points 138.

Five layers can be conceptualized from the inner membrane to the outer membrane, and, for these layers, groups of representative points 130, 132, 134, 136, and 138 are set; that is, individual smoothing processes of the two components are executed for each layer. For example, for the representative point of interest 140, a smoothed vector 150 is defined by the tangential component after the smoothing and the normal component after the smoothing. Reference numeral 148 shows a vector before the smoothing.

In the cardiac muscle region, a plurality of layers arranged in the cardiac muscle transverse direction show different motions from each other. According to the above-described process, a natural smoothing can be performed assuming the motions of the plurality of layers. In other words, excessive smoothing can be avoided.

Figures 11, 12:
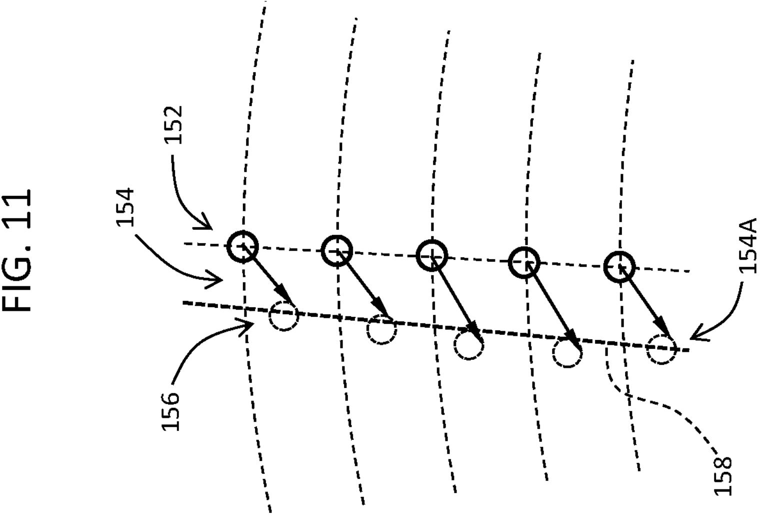
FIG. 11 is a diagram showing a target line in relation to a first alignment method.
FIG. 12 is a diagram showing a representative point sequence after the alignment, in relation to the first alignment method.
Figure 13:
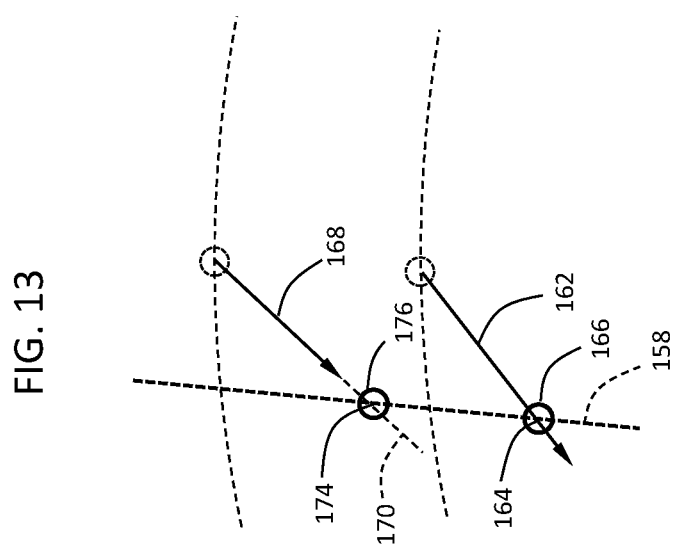

With reference to FIGS. 11 to 17, several alignment methods applied to each representative point sequence will be described. FIGS. 11 to 13 show a first alignment method. In FIG. 11, a representative point sequence 152 on the preceding frame is shown. The representative point sequence 152 is formed from 5 representative points arranged across the cardiac muscle region. For the representative point sequence 152, through the above-described smoothing, a smoothed vector sequence 154 is determined.

The smoothed vector sequence 154 is formed from 5 smoothed vectors originating from the 5 representative points.

In the first alignment method, a method of least squares is applied to a coordinate sequence 154A identified by the smoothed vector sequence 154, and a target line 158 is calculated as a regression line. The target line 158 may also be considered to be an approximated straight line calculated based on a plurality of provisional coordinates. In the method of least squares, a linear function is calculated such that a sum of squares of distances from a plurality of coordinates to the target line is minimized. Reference numeral 156 shows a representative point sequence identified by a vector sequence before smoothing.

As shown in FIG. 12, a plurality of representative points after movement are determined on the target line 158 based on a plurality of smoothed vectors. A new representative point sequence 160 is generated based on the plurality of representative points. In this case, for example, as shown in FIG. 13, if a smoothed vector 162 intersects the target line 158, a representative point 166 may be determined with respect to an intersection 164. On the other hand, if a smoothed vector 168 does not intersect the target line 158, the smoothed vector 168 may be extrapolated to determine an extrapolated line 170, an intersection 174 between the extrapolated line 170 and the target line 158 may be identified, and a representative point 176 may be determined for the intersection 174.

Figure 15:
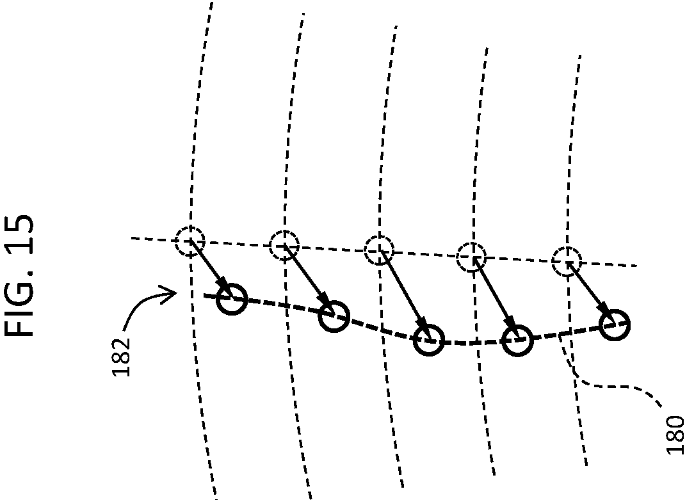
FIG. 15 is a diagram showing a representative point sequence after the alignment, in relation to the second alignment method.
Figure 14:
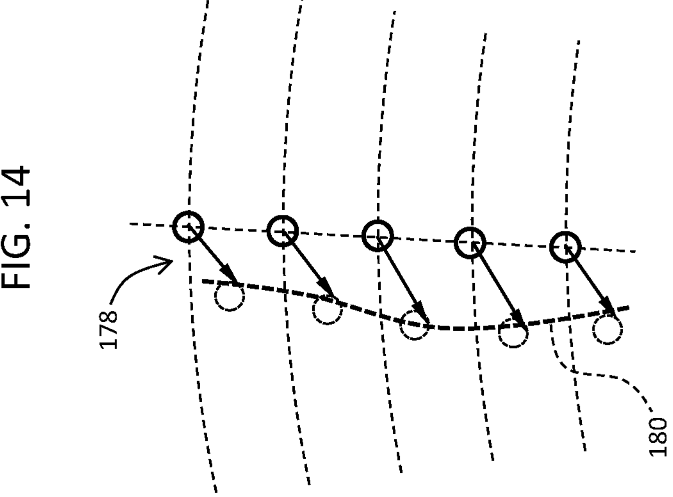
FIG. 14 is a diagram showing a target line in relation to a second alignment method.

FIGS. 14 and 15 show a second alignment method. A target line 180 is determined based on a plurality of coordinates identified by a vector sequence 178 after smoothing. In this case, fitting by a spline function may be performed, or a curved line function may be defined by the method of least squares. As shown in FIG. 15, a plurality of representative points are determined on the target line 180 based on a plurality of vectors after the smoothing. In this case, each intersection may be identified by the method shown in FIG. 13.

Figure 17:
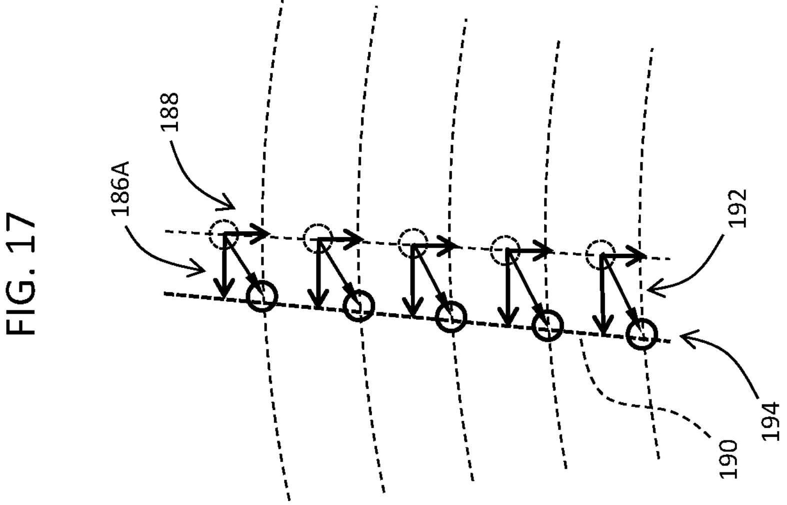
FIG. 17 is a diagram showing a representative point sequence after the alignment, in relation to the third alignment method.
Figure 16:
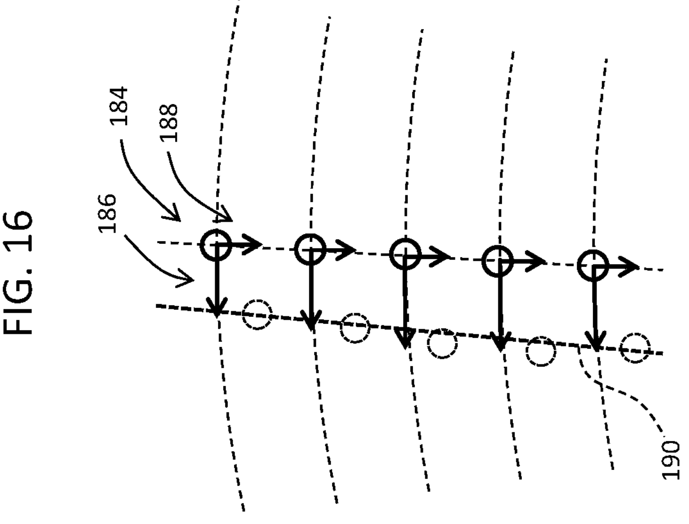
FIG. 16 is a diagram showing a target line in relation to a third alignment method.

FIGS. 16 and 17 show a third alignment method. FIG. 16 shows a smoothed tangential component sequence 186 and a smoothed normal component sequence 188 corresponding to a representative point sequence 184. The method of least squares is applied to the smoothed tangential component sequences 186 among the smoothed component sequences, and a target line 190 is identified as a regression line. As shown in FIG. 17, a size of each smoothed tangential component of the smoothed tangential component sequence is corrected according to the target line, and, with this process, a smoothed tangential component sequence 186A after correction is determined. Based on the smoothed tangential component sequence 186A after the correction and the smoothed normal component sequence 188, a smoothed vector sequence 192 after correction is determined. A plurality of representative points are set on a plurality of coordinates shown by the smoothed vector sequence 192 after the correction. A new representative point sequence 194 is formed from these plurality of representative points.

When the third alignment method is employed, strictly speaking, the plurality of representative points of the new representative point sequence 194 are not positioned on the target line 190, and are not arranged in a straight line. However, the arrangement is an approximate straight line shape, and all of the representative points are positioned near the target line 190. When the third alignment method is employed, an amount of calculation can be reduced.

Figure 18:
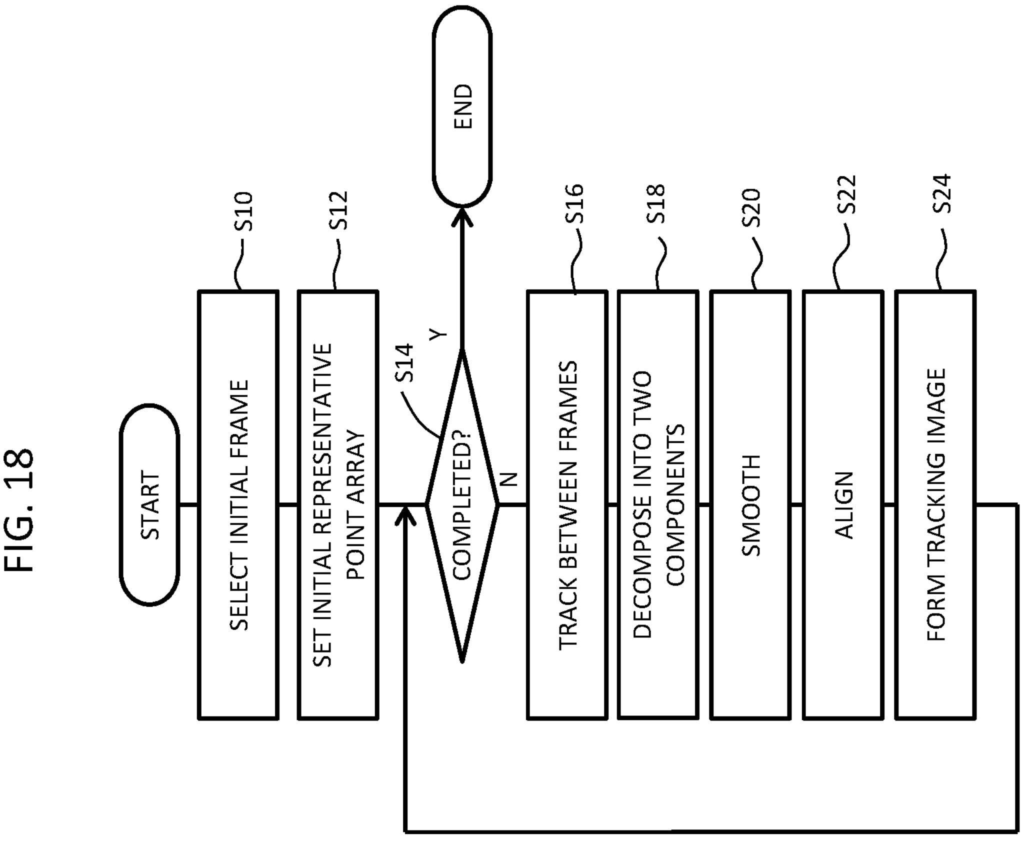
FIG. 18 is a flowchart showing a method of processing an image according to an embodiment of the present disclosure.

FIG. 18 shows an image processing method according to the present embodiment. Typically, a flow shown in FIG. 18 is executed in a frozen state. In S10, an initial frame (starting frame) is selected by an examiner (user). In S12, an initial representative point array is set on the initial frame. In S14, it is judged whether or not the present process is to be completed. For example, the present process is completed when a process of a final frame is completed. A sequence of processes from S16 and later is repeatedly executed between frames in a time sequential order.

In S16, representative points are tracked between designated frames. With this process, a vector array is generated. In S18, each individual vector of the vector array is decomposed into two components (a tangential component and a normal component). In S20, each individual component is smoothed. With this process, a smoothed vector array is generated.

In S22, a new representative point array is generated based on the smoothed vector array. In this process, alignment is performed for each representative point sequence of the new representative point array. In S24, a tracking image is generated based on the new representative point array after the alignment.

According to the above-described embodiment, the vector array is smoothed, and then, when the new representative point array is generated based on the smoothed vector array, each representative point sequence is aligned. Thus, the process tends to not be affected by noise. More specifically, unnatural disturbance and deviation in the tracking image can be effectively suppressed.

The invention claimed is:

1. An ultrasound diagnostic apparatus comprising:

a calculator configured to calculate an (n−1)th vector array (wherein n=1, 2, 3, . . . ) representing two-dimensional movement destinations of an (n−1)th representative point array which is set in a two-dimensional cardiac muscle region between an (n−1)th frame and an nth frame, the two-dimensional cardiac muscle region being a region between an inner membrane of a cardiac muscle and an outer membrane of the cardiac muscle;

a smoother configured to smooth the (n−1)th vector array, to thereby generate an (n−1)th smoothed vector array, the smoother having also been configured to set, for each representative point of interest in the (n−1)th representative point array, a group of representative points including the representative point of interest, the group of representative points being formed from a plurality of representative points arranged along a cardiac muscle contour direction defined in the two-dimensional cardiac muscle region, smooth a plurality of tangential components of a group of vectors belonging to the group of representative points, to calculate a smoothed tangential component for the representative point of interest, smooth a plurality of normal components of the group of vectors belonging to the group of representative points, to calculate a smoothed normal component for the representative point of interest, and generate the (n−1)th smoothed vector array based on the smoothed tangential component and the smoothed normal component forming a smoothed vector for each representative point of interest;

an aligner configured to align, when an nth representative point array formed from a plurality of representative point sequences arranged in the cardiac muscle contour direction is generated in the two-dimensional cardiac muscle region based on the (n−1)th smoothed vector array, each of the representative point sequences comprising three or more representative points arranged along a cardiac muscle transverse direction, the cardiac muscle transverse direction being defined in the two-dimensional cardiac muscle region and intersecting the cardiac muscle contour direction, the aligner having also been configured to calculate, for each representative point sequence of the (n−1)th representative point array, a target line based on a smoothed vector sequence belonging to the representative point sequence or a smoothed tangential component sequence thereof, the target line traversing the two-dimensional cardiac muscle region, and determine, for each representative point sequence of the (n−1)th representative point array, movement destinations of a plurality of representative points of the representative point sequence on or near the target line, to thereby generate the nth representative point array; and a creator configured to create a tracking image based on the nth representative point array, wherein, for each of the representative point sequences, a plurality of groups of representative points which are arranged along the cardiac muscle transverse direction are set.

2. The ultrasound diagnostic apparatus according to claim 1, wherein the target line is a straight line or a curved line.

3. A method of processing an image, the method comprising:

calculating an (n−1)th vector array (wherein n=1, 2, 3, . . . ) representing two-dimensional movement destinations of an (n−1)th representative point array which is set in a two-dimensional cardiac muscle region, based on (n−1)th frame data and nth frame data acquired by transmission and reception of ultrasound, the two-dimensional cardiac muscle region being a region between an inner membrane of a cardiac muscle and an outer membrane of the cardiac muscle;

smoothing the (n−1)th vector array, to thereby generate an (n−1)th smoothed vector array;

setting, for each representative point of interest in the (n−1)th representative point array, a group of representative points including the representative point of interest, the group of representative points being formed from a plurality of representative points arranged along a cardiac muscle contour direction defined in the two-dimensional cardiac muscle region;

smoothing a plurality of tangential components of a group of vectors belonging to the group of representative points, to calculate a smoothed tangential component for the representative point of interest;

smoothing a plurality of normal components of the group of vectors belonging to the group of representative points, to calculate a smoothed normal component for the representative point of interest;

generating the (n−1)th smoothed vector array based on the smoothed tangential component and the smoothed normal component forming a smoothed vector for each representative point of interest;

aligning, when an nth representative point array formed from a plurality of representative point sequences arranged in the cardiac muscle contour direction is generated based on the (n−1)th smoothed vector array, each of the representative point sequences comprising three or more representative points arranged along a cardiac muscle transverse direction, the cardiac muscle transverse direction being defined in the two-dimensional cardiac muscle region and intersecting the cardiac muscle contour direction;

calculating, for each representative point sequence of the (n−1)th representative point array, a target line based on a smoothed vector sequence belonging to the representative point sequence or a smoothed tangential component sequence thereof, the target line traversing the two-dimensional cardiac muscle region;

determining, for each representative point sequence of the (n−1)th representative point array, movement destinations of a plurality of representative points of the representative point sequence on or near the target line, to thereby generate the nth representative point array; and creating a tracking image based on the nth representative point array, for each of the representative point sequences, a plurality of groups of representative points which are arranged along the cardiac muscle transverse direction being set.

4. A non-transitory storage medium storing a program which, when executed, causes an information processing apparatus to execute an image processing method, the program comprising:

a function to calculate an (n−1)th vector array (wherein n=1, 2, 3, . . . ) representing two-dimensional movement destinations of an (n−1)th representative point array which is set in a two-dimensional cardiac muscle region, based on (n−1)th frame data and nth frame data acquired by transmission and reception of ultrasound, the two-dimensional cardiac muscle region being a region between an inner membrane of a cardiac muscle and an outer membrane of the cardiac muscle;

a function to smooth the (n−1)th vector array, to thereby generate an (n−1)th smoothed vector array, the function to smooth having also been configured to set, for each representative point of interest in the (n−1)th representative point array, a group of representative points including the representative point of interest, the group of representative points being formed from a plurality of representative points arranged along a cardiac muscle contour direction defined in the two-dimensional cardiac muscle region, smooth a plurality of tangential components of a group of vectors belonging to the group of representative points, to calculate a smoothed tangential component for the representative point of interest, smooth a plurality of normal components of the group of vectors belonging to the group of representative points, to calculate a smoothed normal component for the representative point of interest, and generate the (n−1)th smoothed vector array based on the smoothed tangential component and the smoothed normal component forming a smoothed vector for each representative point of interest;

a function to align, when an nth representative point array formed from a plurality of representative point sequences arranged in a cardiac muscle contour direction is generated in the two-dimensional cardiac muscle region based on the (n−1)th smoothed vector array, each of the representative point sequences comprising three or more representative points arranged along a cardiac muscle transverse direction, the cardiac muscle transverse direction being defined in the two-dimensional cardiac muscle region and intersecting the cardiac muscle contour direction, the function to align having also been configured to calculate, for each representative point sequence of the (n−1)th representative point array, a target line based on a smoothed vector sequence belonging to the representative point sequence or a smoothed tangential component sequence thereof, the target line traversing the two-dimensional cardiac muscle region, and determine, for each representative point sequence of the (n−1)th representative point array, movement destinations of a plurality of representative points of the representative point sequence on or near the target line, to thereby generate the nth representative point array; and a function to create a tracking image based on the nth representative point array, for each of the representative point sequences, a plurality of groups of representative points which are arranged along the cardiac muscle transverse direction being set.

* * * * *